United States Patent [19]
Errico et al.

[11] Patent Number: 5,733,286
[45] Date of Patent: Mar. 31, 1998

[54] ROD SECURING POLYAXIAL LOCKING SCREW AND COUPLING ELEMENT ASSEMBLY

[75] Inventors: Joseph P. Errico, Far Hills; Thomas J. Errico, Summit; James D. Ralph, Oakland, all of N.J.

[73] Assignee: Third Millennium Engineering, LLC, Summit, N.J.

[21] Appl. No.: 799,722

[22] Filed: Feb. 12, 1997

[51] Int. Cl.$^6$ .................................. A61B 17/70
[52] U.S. Cl. .............................. 606/61; 606/73
[58] Field of Search .................... 606/61, 60, 72, 606/73, 69, 70, 71; 623/17

[56] References Cited

U.S. PATENT DOCUMENTS

| | | | |
|---|---|---|---|
| 4,946,458 | 8/1990 | Harms et al. | 606/61 |
| 5,207,678 | 5/1993 | Harms et al. | 606/61 |
| 5,443,467 | 8/1995 | Biedermann et al. | 606/65 |
| 5,466,237 | 11/1995 | Byrd, III et al. | 606/61 |
| 5,474,555 | 12/1995 | Puno et al. | 606/73 |
| 5,496,321 | 3/1996 | Puno et al. | 606/61 |
| 5,643,261 | 7/1997 | Schafer et al. | 606/61 |

Primary Examiner—Guy V. Tucker
Attorney, Agent, or Firm—Joseph P. Errico, Esq.

[57] ABSTRACT

A polyaxial orthopedic device for use with rod implant apparatus includes a screw having a bowl-shaped head and a coupling element. The coupling element has a rod receiving channel and an axial bore into which the head of the screw may be inserted. The interior surface of the bore is inwardly curvate at the lower end thereof to form a socket for polyaxially retaining the curvate head of the screw. In an initial position the screw head remains polyaxially free with respect to the coupling element. There is also a hemispherical insert which is seated on the top of the screw head, permitting it to rotate, but which may be compressed onto the head to permit the head of the screw to be locked in the bore. The rod is inserted into the channel and a top locking nut or set screw locks presses down on the rod and hemispherical insert to secure the assembly completely.

16 Claims, 2 Drawing Sheets

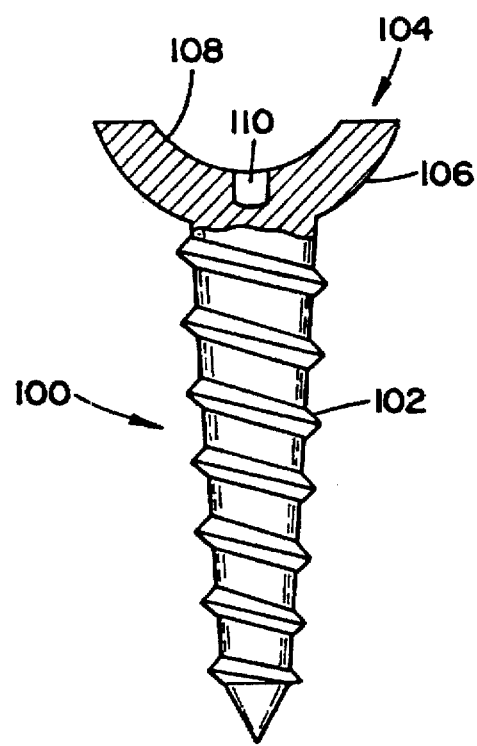
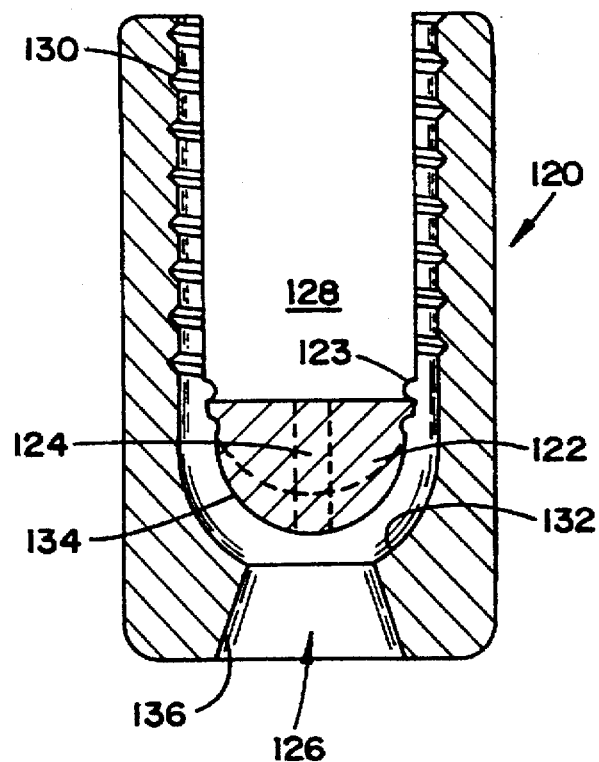
FIG. 1  FIG. 2
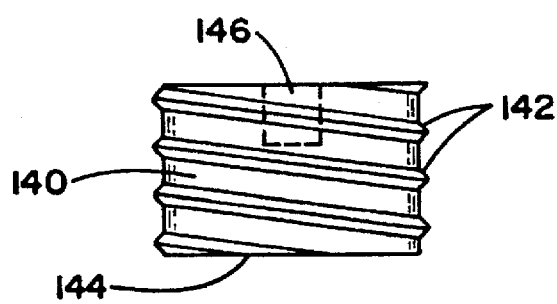
FIG. 3

ROD SECURING POLYAXIAL LOCKING SCREW AND COUPLING ELEMENT ASSEMBLY

BACKGROUND OF THE INVENTION

1. Field of the Invention

This invention relates generally to a pedicle screw having polyaxial rod coupling means for use with orthopedic fixation systems. More particularly, the present invention relates to a screw for insertion into spinal bone, and a coupling element polyaxially mounted thereto for coupling the screw to an orthopedic implantation structure, such as a rod.

2. Description of the Prior Art

The spinal column is highly complex system of bones and connective tissues which houses and protects critical elements of the nervous system and the arterial and veinous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally hooking under the lamina and entering into the central canal, attaching to the transverse process, or coupling through the pedicle bone. The present invention relates to spinal fixation devices for immobilizing and altering the alignment of the spine over a large number, for example more than three or four, vertebra by means of affixing at least one elongate rod to the sequence of selected bones.

Such "rod assemblies" generally comprise a plurality of screws which are implanted through the posterior lateral surfaces of the laminae, through the pedicles, and into their respective vertebral bodies. The screws are provided with coupling elements, for receiving an elongate rod therethrough. The rod extends along the axis of the spine, coupling to the plurality of screws via their coupling elements. The aligning influence of the rod forces the spine to which it is affixed, to conform to a more proper shape.

It has been identified, however, that a considerable difficulty is associated with inserting screws along a misaligned curvature and simultaneously exactly positioning the coupling elements such that the receiving loci thereof are aligned so that the rod can be passed therethrough without distorting the screws. Attempts at achieving proper alignment with fixed screws is understood to require considerably longer operating time, which is known to increase the incidence of complications associated with surgery. Often such alignments, with such fixed axes devices could not be achieved, and the entire instrumentationing effort would end unsuccessfully.

In addition, for many patients specific pathology it is desirable that the rod extend down into and beyond the lumbar portion of the spine, and for the end of the rod to be coupled to the sacral bone. Providing such an end to the assembly in the sacral bone has been understandably suggested inasmuch as it provides superior support to the full extent of the assembly. The most suitable position for the insertion of the screws into the sacral body may not, however, conform to the direction extent of the rod as it is affixed to the entirety of the assembly. Misalignment of the rod with respect to the screw and the coupling element is often a source of considerable disadvantage for the surgeon, often requiring considerable efforts to be expended bending and aligning the rod with the receiving locus of the coupling element. These additional efforts are a considerable difficulty associated with the proper and expeditious affixation, and over the long term, the offset of the rod can have a deleterious effect on the overall performance of the entire implantation assembly.

The art contains a variety of attempts at providing instrumentation which permit a freedom with respect to angulation of the screw and the coupling element. These teachings, however, have generally been complex, and inadequately reliable with respect to durability. The considerable drawbacks associated with the prior art systems include complexity, difficulty properly positioned the rod and coupling elements, and the tedious manipulation of the many parts associated with the complex devices.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a polyaxial locking screw and coupling element for use with rod stabilization and immobilization systems in the spine. More particularly, the polyaxial screw and coupling element assembly of the present invention comprise a bone screw having a head which is bowl-shaped, a coupling element mounted thereon so as to be free to rotate prior to the secure fixation of the rod thereto, and a curvate insert which seats in, and is free to rotate within, the bowl shaped recess of the head. The rod seats in the head, on the curvate insert, and is locked in place by a top locking nut. The top locking nut applies a downward force on the insert, which in turn compresses the head within the coupling element to securely lock the assembly together. The relative geometries of the elements, however, permits this locking to occur through a range of polyaxial positions such that the rod may be captured and secured by the coupling element with the coupling element at a variety of angles relative to the screw.

More specifically, the screw comprises a standard bone screw, having a threaded shaft for insertion into the bone. The head of the screw, however, is bowl shaped, having a widened top portion which has a convex curvature on the underside thereof, and a concave recess formed in the top. It is preferable that each of the curvatures (the underside and the recess) comprise constant radii curvatures, thereby being spherical sections. In addition, it is most preferable that the curvatures be concentric as well.

The coupling element comprises a tubular section having a channel formed in the top thereof, into which a rod may be received. As a tubular element, the coupling element includes a bore which is axially disposed. The bottom portion of the bore is inwardly tapered with a curvature of the taper being substantially equal to the curvature of the underside of the screw head. The shaft of the screw is more narrow than the bottom opening so that, when the head is seated in the bottom of the coupling element, the screw and coupling element may polyaxially rotate relative to one another.

A hemispherical insert is provided to be placed in the coupling element, so that it may float in the concave recess at the top of the screw when the screw is positioned in the bottom of the bore. This insert may be retained in place within the bore by a variety of different means, including but not limited to, a retaining ring, an annular lip, a set screw, etc. The hemispherical insert must, however, be permitted to translate downward, into the recess of the screw head. It shall, therefore, be understood that the hemispherical insert floats in the recess of the screw head prior to being compressed thereinto. The screw may rotate relative to the coupling element, and relative to the hemispherical insert. The insert is compressed by the insertion of a rod into the coupling element, and the subsequent locking of the rod in place provides the downward force to compress the insert into the screw head, independent of the relative angle thereof, and the screw head into the bottom of the bore, thus locking the assembly in place at whatever angle the structure may have been in at the time.

The preferred method of construction is to form the coupling element of a straight tubular material, to form or place the necessary retaining means in the axial bore to hold the hemispherical insert in place, to insert the screw with the appropriately formed head into the assembly from the bottom, and then the "coin", or roll, the bottom portion of the coupling element between compression rollers so that the bottom of the element is curvate as specified above.

In an perferred embodiment, the hemispherical insert and the head of the screw include a central axis hole through which a screw driving tool may be inserted to drive the screw into the appropriate spinal bone.

Multiple screw and coupling element assemblies are generally necessary to complete the full array of anchoring sites for the rod immobilization system, however, the screw and coupling element assembly of the present invention is designed to be compatible with alternative rod systems so that, where necessary, the present invention may be employed to rectify the failures of other systems the implantation of which may have already begun.

BRIEF DESCRIPTION OF THE FIGURES

FIG. 1 is a side view of a screw having a bowl-shaped curvate head which is an aspect of the present invention.

FIG. 2 is a side view of the coupling element of present invention and the hemispherical insert, wherein critical interior features of the structure are shown in phantom.

FIG. 3 is a side cross-sectional view of the top set screw of the present invention.

DETAILED DESCRIPTION OF THE PREFERRED EMBODIMENT

Figure 4:
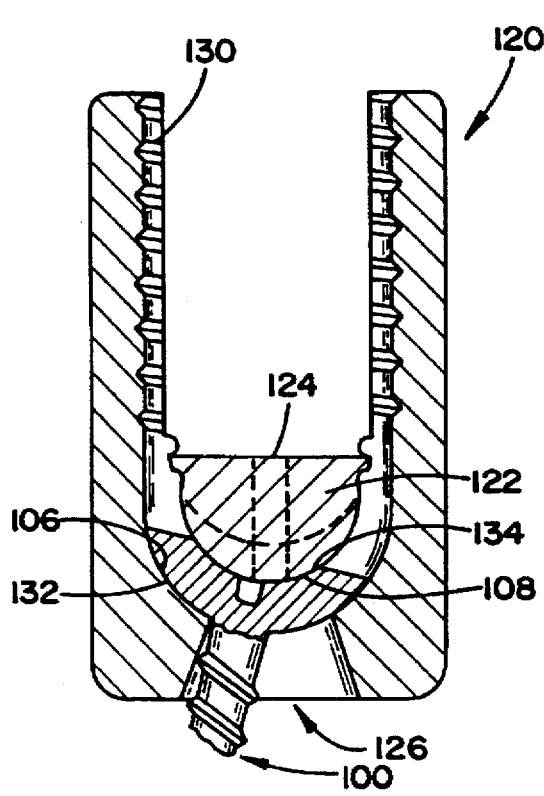
FIG. 4 is a side view of the coupling element of the present invention, as shown in FIG. 2, wherein the curvate head of a polyaxial screw, as shown in FIG. 1, is positioned within the lower socket portion thereof.

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Referring now to FIG. 1, a side view of the screw portion of the present invention, comprising a bowl-shaped head, is shown. The screw 100 comprises a a threaded shaft 102 and a curvate head 104. The curvature of the undersurface 106 of the head 104 is convex, and is preferably a curvature of constant radius (therein being a section of a sphere). The inner surface 108 of the head 104 is concave, and is also preferably has a constant radius of curvature so as to also be a section of a sphere. It is particularly preferable that the surface curvatures be concentric, and that the mutual center of the curvatures be along the long axis of the shaft 102. It is also desirable that the curvatures be symmetric about the central axis.

In addition, the head 104 includes a central, axial hole 110 formed in the base of the head 104 of the screw 100 which permits a screwdriver tool so that the screw 100 may be easily driven into a spinal bone.

Referring now to FIG. 2, the coupling element 120 is provided with the hemispherical insert 122 positioned in place within the axial bore 126 thereof, and retained by a pair of internally directed flange elements 123. The hemispherical insert 122 has an underportion 134 which is convexly hemispherical and also includes through hole such that a screwdriving tool may be inserted therethrough so that it may access the hole 110 in the head 104 of the screw 100 which is to be positioned thereunder. The relative position of the hemispherical insert 122 and the flanges 123 are provided such that the head 104 of the screw 100, when positioned thereunder, may rotate polyaxially.

With respect to the coupling element 120 itself, the structure is substantially tubular with a rod receiving channel 128 formed in the top thereof. The interior of the top portion includes a threading 130 (which threading may alternatively be provided on the outer upper surface of the coupling element as well) for receiving a set screw (or locking nut).

The lower portion of the axial bore includes a curvate taper 132 which preferably has the identical radius of curvature of the undersurface 106 of the head 104 of the screw 100. The radius of curvature of the undersurface 134 of the hemispherical insert is preferably equal to the radius of curvature of the top surface 108 of the head 104 of the screw 100. The bottom opening 136 of the axial bore 126 is larger than the shaft 102 of the screw 100, but is less than the diameter of the head 104, so that the head can be nested in the bottom of the bore 126, with the undersurface 106 of the head 104 slideably (initially) nested against the tapered interior surface 132 of the bore (see FIG. 4).

Referring now to FIG. 3, the set screw 140 of the present invention is provided in a side cross-section view. The set screw 140 has a cylindrical body having a threading 142 thereon. The threading 142, and the diameter of the set screw 140 itself, are designed to seat in the axial bore 126 of the coupling element 120 and mate the the threading 130 therein. (It shall be understood that the set screw 140 is replaced by a locking nut in the embodiment of the present invention wherein the threading of the coupling element is provided on the exterior surface of the element). The set screw further includes a flat, or ridged underside 144 which is ideally suited to gripping a rod surface. The upper portion of the set screw includes a recess 146 into which a screw driving tool may be inserted to drive the set screw into the coupling element.

Referring now to FIG. 4, in which the assembly of the screw 100 and the coupling element 120 is provided, the assembly and function and function of the device is hereinbelow described. The preferred method of assembly of the present invention is to form the coupling element 120 of a tubular preform and to form the necessary flange elements 123 within the bore 126 at the proper position. The hemispherical insert 122 is then placed in the bore 126 followed by the head 104 of the screw 100. The lower exterior of the coupling element 120 is then coined, or rolled, until the lower inner surface 132 of the bore 126 is properly curved as set forth more fully above. In this position, the screw 100 may rotate polyaxially relative to the coupling element 120 as the head slides between the lower inner surface 132 of the coupling element 120 and the undersurface 134 of the hemispherical insert 122.

Figure 5:
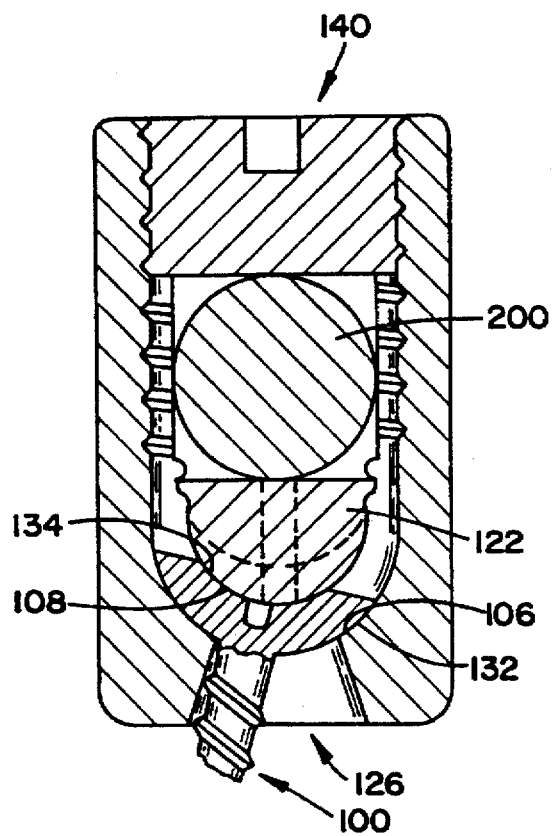
FIG. 5 is a side cross-sectional view of the present invention in its fully assembled disposition having a rod securely locked therein.

Referring now also to FIG. 5, in which the assembly has been locked together with a rod 200 in the channel 128 of the coupling element 120, the continued assembly and function of the invention is set forth herein below. Once the screw 100 and the coupling element 120 have been assembled, the surgeon may align the holes 124,110 in the hemispherical insert 122 and the head 104, respectively, and drive the assembly into the spinal bone of the patient. Removal of the screw driving tool releases the coupling element 120 to rotate freely on the head 104 of the screw 100, constrained only by the shaft 102 of the screw 100 contacting the surface 136 of the bottom of the bore 126 at the extreme range of the rotation. The head 104 of the screw also floats beneath the undersurface 134 of the hemispherical insert 122.

Once the surgeon has properly positioned the coupling element 120, the rod 200 is placed in the channel 128, and seated against the top of the hemispherical insert 122. The subsequent insertion and tightening of the set screw 140 downward onto the rod 200 causes the rod 200 to compress against the hemispherical insert 122, and in turn, compresses the head 104 of the screw 100 against the tapered inner surface 132 of the bore 126. The geometry of the assembly permits secure locking of the head 104 in the bore 100 independent of the angle the coupling element 120 has been polyaxially rotated to relative to the screw 100. The assembly is thereby securely locked in position.

While there has been described and illustrated embodiments of a polyaxial screw and coupling element assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A polyaxial screw and coupling element assembly for use with orthopedic rod implantation apparatus, comprising:
   a screw having a curvate head, said head including a concave spherical recess and a convex spherical undersurface;
   a coupling element including a rod receiving channel, a threaded portion, and an axial bore having an inwardly spherically curvate surface lower end, said inwardly curvate surface defining a socket wherein said undersurface of said head of said screw may nest such that the screw and head may polyaxial rotate relative to one another;
   a hemispherical insert positioned in the bore of said coupling element and seated in the concave spherical recess in the head of the screw, such that said hemispherical insert remains rotationally stable relative to the coupling element, but such that said insert may translate axially relative to said bore, while the screw is polyaxially rotated relative to the coupling element; and
   a locking means, mateable with said threaded portion of said coupling element, for locking a rod in said channel, said locking means further providing a downward translational force onto the hemispherical insert which in turn compresses into the concave recess in the head of the screw, which supplies the compressive locking force to securely crush lock the head in the bottom of the bore of the coupling element, whereby the assembly is securely prevented from further relative motion.

2. The assembly as set forth in claim 1, wherein said threading is formed on an upper surface of said bore.

3. The assembly as set forth in claim 2, wherein the locking means comprises a set screw.

4. The assembly as set forth in claim 1, wherein said threading is formed on an upper exterior surface of said coupling element.

5. The assembly as set forth in claim 4, wherein said locking means comprises a top locking nut.

6. The assembly as set forth in claim 1, wherein said coupling element further includes means for retaining said hemispherical insert in said bore.

7. The assembly as set forth in claim 6, wherein said retaining means comprises at least one inwardly directed flanges.

8. The assembly as set forth in claim 6, wherein said bore of said coupling element includes an annular recess formed therein, and said retaining means comprises an expandable retaining ring.

9. An orthopedic rod implantation apparatus, comprising:
   at least one elongate rod;
   at least one polyaxial screw and coupling element including
      a screw having a curvate head, said head including a concave spherical recess and a convex spherical undersurface,
      a coupling element including a rod receiving channel, a threaded portion, and an axial bore having an inwardly spherically curvate surface lower end, said inwardly curvate surface defining a socket wherein said undersurface of said head of said screw may nest such that the screw and head may polyaxial rotate relative to one another,
      a hemispherical insert positioned in the bore of said coupling element and seated in the concave spherical recess in the head of the screw, such that said hemispherical insert remains rotationally stable relative to the coupling element, but such that said insert may translate axially relative to said bore, while the screw is polyaxially rotated relative to the coupling element, and
      a locking means, mateable with said threaded portion of said coupling element, for locking the rod in said channel, said locking means further providing a downward translational force onto the hemispherical insert which in turn compresses into the concave recess in the head of the screw, which supplies the compressive locking force to securely crush lock the head in the bottom of the bore of the coupling element, whereby the assembly is securely prevented from further relative motion.

10. The assembly as set forth in claim 9, wherein said threading is formed on an upper surface of said bore.

11. The assembly as set forth in claim 10, wherein the locking means comprises a set screw.

12. The assembly as set forth in claim 9, wherein said threading is formed on an upper exterior surface of said coupling element.

13. The assembly as set forth in claim 12, wherein said locking means comprises a top locking nut.

14. The assembly as set forth in claim 13, wherein said coupling element further includes means for retaining said hemispherical insert in said bore.

15. The assembly as set forth in claim 14, wherein said retaining means comprises at least one inwardly directed flanges.

16. The assembly as set forth in claim 14, wherein said bore of said coupling element includes an annular recess formed therein, and said retaining means comprises an expandable retaining ring.

\* \* \* \* \*